(12) United States Patent
Binder et al.

(10) Patent No.: US 8,637,282 B2
(45) Date of Patent: Jan. 28, 2014

(54) PROCESS FOR FRACTIONATION OF LIGNOCELLULOSIC BIOMASS

(75) Inventors: Thomas P. Binder, Decatur, IL (US); Paul D. Bloom, Forsyth, IL (US); Perry H. Doane, Decatur, IL (US); Chi-Cheng Ma, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 13/521,469

(22) PCT Filed: Jan. 21, 2011

(86) PCT No.: PCT/US2011/022000
§ 371 (c)(1),
(2), (4) Date: Sep. 21, 2012

(87) PCT Pub. No.: WO2011/097075
PCT Pub. Date: Aug. 11, 2011

(65) Prior Publication Data
US 2013/0011885 A1    Jan. 10, 2013

Related U.S. Application Data

(60) Provisional application No. 61/300,855, filed on Feb. 3, 2010.

(51) Int. Cl.
*C12P 7/10* (2006.01)

(52) U.S. Cl.
USPC .......................................................... 435/165

(58) Field of Classification Search
USPC .......................................................... 435/165
See application file for complete search history.

(56) References Cited

U.S. PATENT DOCUMENTS 5,562,777 A * 10/1996 Farone et al. .................... 127/37
2009/0286295 A1* 11/2009 Medoff et al. ................. 435/162

* cited by examiner

*Primary Examiner* — Ralph Gitomer
(74) *Attorney, Agent, or Firm* — William B. Miller (57) ABSTRACT

Methods are provided for the efficient fractionation of lignocellulosic biomasses into cellulosic, hemicellulosic and lignin fractions, wherein concentrated organic acid vapors are applied to the biomass at elevated temperatures at the location(s) or near the location(s) where the biomass has been harvested and gathered, to at least partly depolymerize or substantially solubilize the hemicelluloses and lignins in the biomass. The organic acid-treated biomass is in either case then dried and pelletized for extended bulk storage and/or for shipment to a second facility some distance away. The organic acid-treated biomass may be processed into desired chemicals, fuels and/or fuel additives at the local processing site or at a second facility away from the local processing site, or the pelletized material may be used as a ruminant feed locally or at a feedlot some distance removed from the local processing site.

36 Claims, 3 Drawing Sheets

PROCESS FOR FRACTIONATION OF LIGNOCELLULOSIC BIOMASS

This application is a National Stage application filed under Rule 371 based upon PCT/US11/22000 filed Jan. 21, 2011 which claims benefit of provisional application 61/300,855 filed Feb. 3, 2010.

This invention concerns an improved process for accomplishing the fractionation of lignocellulosic biomass, especially for further use in the synthesis of chemicals or the preparation of biobased fuels or fuel additives.

The use of biomass—of materials whose carbon content is of biological rather than fossil origin—for providing chemicals and fuel products presently derived from fossil-origin materials such as petroleum, or for providing acceptable biobased, functional alternatives to such chemicals and fuel products, has increasingly become a focus of research and development investment and effort in recent years as supplies of fossil-origin materials have been compromised or been more difficult or expensive to acquire and use.

Certain chemical and fuel product replacements or alternatives are already produced on a large, commodity scale from biomasses. For the liquid fuel products area, ethanol and biodiesel (fatty acid alkyl esters) have heretofore been produced on a commodity scale from corn and sugar cane (for ethanol) and from various vegetable oils and fats. Even for these examples, though, there remains room for improvements in biomass utilization.

It has been long recognized, for instance, that it would be preferable to be able to make suitable liquid fuels and fuel additives (or equally bioderived, nonfuel chemicals of interest) from lignocellulosic biomasses not substantially used as food products, or which can be harvested or sourced and used without materially adversely affecting land use patterns and behaviors (for example, deforestation to produce additional soy, corn or like crops). A number of non-food, lignocellulosic biomasses might be contemplated of this character, including, for example, purpose-grown non-food biomass crops (such as grasses, sweet sorghum, fast growing trees), or more particularly wood wastes (such as prunings, wood chips, sawdust) and green wastes (for instance, leaves, grass clippings, vegetable and fruit wastes). As well, it has been estimated that as to lands already under cultivation about three quarters of the biomass generated is waste, so that whether the biomass in question is waste the various chemical and fuel products of interest that could be made starting with lignocellulosic biomasses, should in fact be capable of being made economically.

Unfortunately, the truth of the matter is that there are a number of practical, real-world difficulties that must be overcome in order for this proposition to hold true. A first difficulty arises from the very different characteristics of the various components comprising lignocellulosic biomasses.

In this regard, as is true of fossil-based materials such as petroleum, the practical capability of producing the full range of commodity chemicals and fuel product replacements or alternatives that are or will be needed, on the scale and with the qualities, economy and efficiency that are needed, depends for the lignocellulosic biomasses on whether the biomasses can be thoroughly and efficiently fractionated into their various component parts so that these can be used directly or converted into other useful forms. For petroleum, of course, this fractionation occurs in a refinery through various processes, but similar processes have not been developed to date for the lignocellulosic biomasses.

With respect to the present invention, lignocellulosic biomasses are comprised mainly of cellulose, hemicellulose and lignin fractions, with cellulose being the largest of these three components. Cellulose derives from the structural tissue of plants, and consists of long chains of beta glucosidic residues linked through the 1,4 positions. These linkages cause the cellulose to have a high crystallinity. Hemicellulose by contrast is an amorphous heteropolymer, while lignin is an aromatic three-dimensional polymer interspersed among the cellulose and hemicellulose within a plant fiber cell.

Parenthetically in regards to the lignin fraction, the materials understood as encompassed within the term "lignin" and the method by which lignin content has been correspondingly quantified in a biomass have historically depended on the context in which the lignin content has been considered, "lignin" lacking a definite molecular structure and thus being determined empirically from biomass to biomass. In animal science and agronomy, in considering the digestible energy content of lignocellulosic biomasses, for example, the amount of lignin in a given biomass has more commonly been determined using an acid detergent lignin method (Goering and Van Soest, *Forage Fiber Analyses (Apparatus, Reagents, Procedures, and Some Applications)*, Agriculture Handbook No. 379, Agricultural Research Service, United States Dept of Agriculture (1970); Van Soest et al., "Methods for Dietary Fiber, Neutral Detergent Fiber, and Nonstarch Polysaccharides in Relation to Animal Nutrition", J. Dairy Sci., vol. 74, pp 3583-3597 (1991)). In the paper and pulp industry, by contrast, the amount of lignin in a given biomass has been conventionally determined by the Klason lignin method (Kirk and Obst, "Lignin Determination", Methods in Enzymology, vol 16, pp.: 89-101 (1988)).

As a frame of reference for the present invention, an acid detergent insoluble lignin content of 6% or more (on a dry weight basis) is generally consistent with mature temperate grasses having relatively low nutritive value for ruminants and which consequently are diverted to other uses in the main. It is with lignocellulosic biomasses of this general character with which the present invention in most directly concerned, then, though the improvements provided by the present invention will be useful for the full range of lignocellulosic biomasses generally.

Because of the differences in the cellulosic, hemicellulosic and lignin fractions of biomass, as well as considering other lesser fractions present in various biomasses to different degrees, as related in U.S. Pat. No. 5,562,777 to Farone et al., "Method of Producing Sugars Using Strong Acid Hydrolysis of Cellulosic and Hemicellulosic Materials", a number of processes have been developed or proposed over the years to fractionate lignocellulosic biomasses, Most involve hydrolyzing the cellulosic and hemicellulosic fractions into C6 and C5 sugars.

Fundamentally both biological and non-biological processes have been disclosed, with the oldest and best known non-biological methods of producing sugars from cellulose involving acid hydrolysis, most commonly sulfuric acid-based hydrolysis using a dilute acid approach, a concentrated acid approach or a combination of the two. The '777 patent to Farone et al. describes the advantages and disadvantages of the various sulfuric acid-based processes then known to the art, and suggests a further variation using strong acid/sulfuric acid hydrolysis and employing one or more iterations of a combination of a decrystallization step wherein the biomass (and/or including the solids left from the decrystallization step in a previous iteration) is mixed with a 25-90 percent sulfuric acid solution to solubilize a portion of the biomass, then the acid is diluted to between 20 and 30 percent and the mixture heated to preferably between 80 and 100 degrees Celsius for a time to solubilize the cellulosic fraction and any hemicellulosic material that had not been hydrolyzed.

Even given an effective fractionation method, a further challenge posed by the proposed conversion of lignocellulosic biomasses into chemicals, fuels and fuel additives comes simply from the logistics of either a) having to harvest or collect very large amounts of agricultural residues from a large geographic area, for example, and then ship these to large scale chemical or petrochemical processing and distribution hubs located typically some distance away, or b) constructing a local facility for preliminarily processing the biomass to intermediates that are less affected by storage and shipment conditions than the biomass would be (affected) and that are otherwise better suited to being shipped to a processing and distribution hub for chemicals and fuels, for example, C5 and C6 sugars in a syrup or C5 and C6 sugar alcohols/polyols or c) constructing a number of smaller greenfield plants for producing the finished chemicals, fuels or fuel additives adjacent sources of lignocellulosic biomass. Option b) is understood as being preferable to either a) or c), but the lignocellulosic biomass refining concepts proposed to date still unfortunately contemplate intermediates that would prove difficult to ship economically.

Still a further difficulty arises from the fact that these biomasses derive from living matter. In any transformative process, consistency of the feedstock is always a concern, and because the biomasses derive from living organisms feedstock quality will inherently be somewhat changeable and will present particular challenges in terms of feedstock consistency for their harvesting, storage and transport.

The present invention provides methods for processing lignocellulosic biomasses in ways that can address and overcome some or all of the above-mentioned difficulties.

For example, the present invention in a first method provides for the efficient fractionation of lignocellulosic biomass into cellulosic, hemicellulosic and lignin fractions, wherein concentrated organic acid vapors are applied to the biomass at elevated temperatures at the location(s) or near the location(s) where the biomass has been harvested and gathered, to at least partly depolymerize the hemicelluloses and lignins in the biomass. The organic acid-treated biomass is then dried to an extent whereby the dried solids can be pelletized for extended bulk storage or shipment to a second facility located nearer a source of demand or nearer distribution means for the desired chemicals, fuels or fuel additives or making use of an existing chemicals or fuels processing facility. Alternatively, the material may be stored and subsequently processed into the desired chemicals, fuels and/or fuel additives at the local processing site, or the second facility in question (whether adjacent, near or remote) can be a feedlot for ruminants and the pelletized material may be used as a ruminant feed.

For production of fuels, fuel additives and chemical products at a second facility, the at least partly depolymerized hemicelluloses and salts are recovered as one fraction by dissolving the same in a suitable solvent with filtering, the solvent typically being hot water since the lignin fraction is substantially water-insoluble, and the at least partly depolymerized lignins fraction is recovered in turn by dissolution in a more highly concentrated organic acid or other suitable solvent and filtration. The remaining solids comprise a substantially clean cellulose pulp. The hemicellulosic, cellulosic and lignin-derived fractions may then be further processed for making fuels, fuel additives or other desirable chemical products as further described below.

In an alternative embodiment, hemicelluloses and lignins in the lignocellulosic biomass are substantially solubilized by exposure to typically more concentrated organic acid vapors at elevated temperatures, and then are separated from the remaining predominantly cellulosic solids fraction at the local processing facility by washing with a suitable solvent and with filtration. The remaining solids are subsequently dried and preferably pelletized to provide a dried, compacted cellulose fraction that can be stored for local processing or more conventionally shipped as before to a second facility located nearer a source of demand or nearer distribution means for the desired chemicals, fuels or fuel additives or making use of an existing chemicals or fuels processing facility. The remaining solids may also be pelletized and provided to a feedlot for ruminants (as an alternate second facility) for use as a feed, rather than as a material from which fuels, chemicals or fuel additives are to be made.

In a variation of the second embodiment, the solubilized hemicelluloses and lignins may themselves be reduced by evaporation to a mixed solid that can be pelletized and economically shipped to a second facility or in the alternative stored and subsequently processed locally, with the further processing in either case involving separating the hemicellulose and lignin components by extracting the hemicellulose component into a solvent (or solvent mixture) which is effective for dissolving the hemicelluloses but in which the lignin fraction is substantially insoluble, a suitable solvent being simply water, and then processing some or all of the hemicellulosic, cellulosic and lignin-derived fractions to yield the desired chemicals, fuels or fuel alternatives.

Organic acids, including especially formic acid, have long been used in the pulp and paper industry to process lignocellulosic biomasses. Current pulping processes typically use concentrated formic acid solutions in water (80 to 90 percent formic acid, for example) at temperatures of from 90 to 150 degrees Celsius, and at a solvent:biomass solids ratio of 4:1 or greater, to solubilize the lignin and lower molecular weight hemicelluloses in the biomass (through depolymerization) so these can be subsequently removed. The desired cellulosic pulp solids are separated from the cooking liquor containing the lignin and hemicelluloses, then washed and bleached as desired, while the lignin and hemicelluloses can subsequently themselves be separated by adding water, in that the lignin is substantially insoluble in water whereas the hemicelluloses are soluble.

While concentrated formic acid is effective at dissolving and separating out both the lignin and hemicellulose components from the cellulose component of a lignocellulosic biomass, the process uses considerable energy for heating large enough amounts of formic acid and water to generate the pulp slurry, and removal and recovery of the formic acid in high enough concentrations for solvent recycle is difficult and costly due to the formation of azeotropes with water, acetic acid and formic acid.

With regard to the use of lignocellulosic biomasses for synthesis of chemicals or the preparation of biobased fuels or fuel additives, however, the energy consumption and solvent (plus solvent recovery) demands associated with these known organic acid-based fractionation processes would make the costs of producing the chemicals, biobased fuels or fuel additives impractically high, as compared to the costs to produce such materials starting from petroleum.

By accomplishing the solubilization of hemicelluloses and lignin into readily extractable fractions through the use of hot organic acid vapors permeating through the biomass, in contrast, there is no need with the present invention to process the same large quantities of formic acid and water as used in the prior pulping processes. Moreover, we have found that lesser concentrations of formic acid can be used as compared to the conventional, liquid-based formic acid fractionation methods, further reducing the formic acid recovery requirements of the fractionation. The formic acid that is used may be recovered by azeotropic distillation as contemplated in a pulping type application. Alternatively, precisely because of the smaller amounts of water and acid involved, the formic acid that is sought to be recovered for recycle can be recovered simply and without need for breaking the water-formic acid azeotrope, through the use of organic co-solvents we have identified and through simple distillation. And, of course, because of the comparatively much smaller amounts of organic acid used in our process to accomplish the fractionation for further processing of a lignocellulosic biomass as compared to the previously-known pulping processed, the organic acid that remains after the fractionation has been accomplished may (on a consideration of the expense of recovering the acid) also be simply neutralized in whole or in part.

Figure 1:
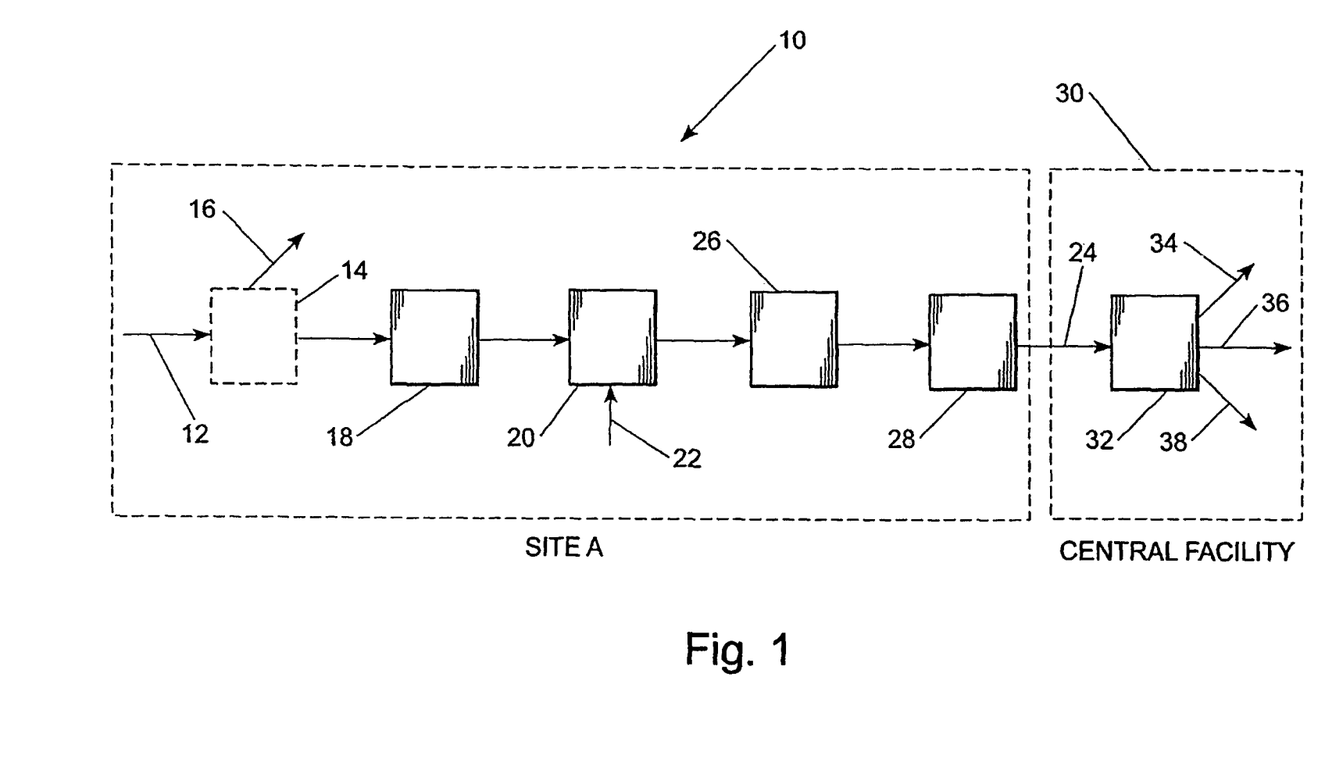
FIG. 1 is a schematic drawing illustrating a process according to the present invention, in one embodiment.

The present invention may be more readily understood by reference to FIG. 1, which schematically depicts a process of the present invention in a preferred embodiment (10). A lignocellulosic biomass 12, typically containing 6 percent or more of acid detergent insoluble lignin (on a dry weight basis), is initially preferably collected and washed as necessary to remove dirt and other contaminants at a location (Site A) that is convenient to where the biomass is produced or generated, then optionally preprocessed in step 14 to isolate a component higher in protein that may be desirable for animal feed or fertilizer (by mechanically breaking down the biomass and by air classification, as one example) and/or to isolate a component or components 16 which have a comparatively high content of a species or material that will be more difficult to remove downstream, and that may interfere with or make intended downstream conversions more difficult and/or may adversely affect the contemplated products from further processing (for example, nitrogen compounds, sulfur compounds, higher ash components). An example of a component in a promising biomass that would be desirably removed in a preprocessing step 14 would be the leaf fraction from corn stover, which is higher in nitrogen but has the approximate nutritional value of hay when considered as a ruminant feed.

After optionally preprocessing the biomass 12 in step 14, the biomass 12 (or the remainder of biomass 12 after the optional removal of component(s) 16) is preferably further prepared/preprocessed in step 18 for being subsequently contacted with the hot concentrated organic acid vapors 22 in step 20. The preprocessing in step 18 includes mechanically breaking down the biomass 12 to allow the concentrated acid vapors 22 to more readily permeate the biomass 12 and at least partly depolymerize or substantially solubilize lignin and hemicelluloses in the biomass 12, to the extent this has not been accomplished in step 14. As well, step 18 may involve drying the biomass 12 to a moisture content of preferably 10 percent or less, though those skilled in the art will understand that the level of moisture in the acid steeping step 20 may be managed by other means as well, including for example through the concentration and amounts supplied of the concentrated hot organic acid vapors 22. Any number of means are known to those skilled in the art for mechanically breaking down the biomass in step 18, for example and without limitation, grinding, chopping and hammermilling, and it will be well within the capabilities of those skilled in the art to select means to break down the biomass 12 whereby the lignin and hemicelluloses therein can be at least partly depolymerized or substantially solubilized by efficient and effective contact with the hot concentrated organic acid vapors 22 in step 20.

The biomass 12 can as indicated above be any lignocellulosic biomass, but as previously noted will preferably not be substantially used as a food source for humans and more preferably will be a biomass that is readily available (or can be made readily available) in those places with the greatest demand for the chemicals, biobased fuels and fuel alternatives to be made from the biomass. Mature grasses, grain crop residues separately or as contained in a grain silage, corn stover, wheat straw, barley straw, miscanthus specie, switchgrass, bahia grass, sorghum specie, sugar cane bagasse, orchardgrass, reed canarygrass and cotton gin trash are exemplary biomasses that may be considered. Mixtures of biomasses from various sources, including biomasses from the harvesting and processing of food crops, are obviously contemplated as well and should be considered as encompassed by the use of the singular "a biomass" and "a lignocellulosic biomass". Whole plant silage, for example, whole plant corn harvested and stored largely anaerobically/ensiled to form silage, would be contemplated as a kind of mixed biomass feed, and is of interest in that most facilities for making renewable source-based chemicals, fuels and fuel additives will require year-round access to the biomass or biomass-based feeds to those facilities. Where several different biomasses are employed from various sources, preferably a purpose-grown non-food biomass or an agricultural waste biomass comprises the largest fraction of those several biomasses in the mixture. An example of a mixed biomass feed would be comprised of corn stover and corn fiber, with preferably corn stover comprising a greater proportion of the feed than the corn fiber.

Parenthetically, those skilled in the art will appreciate that certain biomasses may be more suited to making certain chemicals, fuels and additives (or a certain slate of products in desired proportions) than others, but an advantage of the present invention is its adaptability to the fractionation of lignocellulosic biomasses generally, and as will be seen, especially of biomasses which otherwise might not be considered viable because of their remoteness to a facility for producing the desired chemicals, fuels and/or fuel additives.

Returning now to FIG. 1, depending in part on the concentration of acid used, in the acid vapor steeping step 20 the hot concentrated organic acid 22 acts to at least partly depolymerize hemicelluloses and lignin in the biomass from preprocessing step 18 or substantially solubilizes the lignin and lower molecular weight hemicelluloses and provides a liquid and residual fiber solids which include the cellulose fraction of the biomass. Preferably the concentrated acid vapors 22 are vapors of an organic acid, such as acetic, propionic, malic, succinic or formic acid, or consist of a mixture of such acids. Most preferably, concentrated formic or acetic acid vapors 22 are employed, with the acid being present at from 50 up to 90 volume percent and more, with water vapor being the balance.

We have found in this regard that a vapor of 50 percent or more of acetic acid in water can, with sufficient heating and time in contact with a well-divided and mixed corn stover biomass, be sufficient to depolymerize hemicellulosic and lignin materials in the stover to an extent whereby the partly depolymerized materials can serve as a binder for the pelletized material 24 resulting from the drying and pelletization or densification steps 26 and 28, respectively. Preferably, no additional binders are required to achieve pellets having the desired durability for extended bulk storage locally or for transport to a second location for use as a ruminant feed or for further fractionation and processing in a second or central facility (labeled as such in the drawings), as further discussed below.

Figure 2:
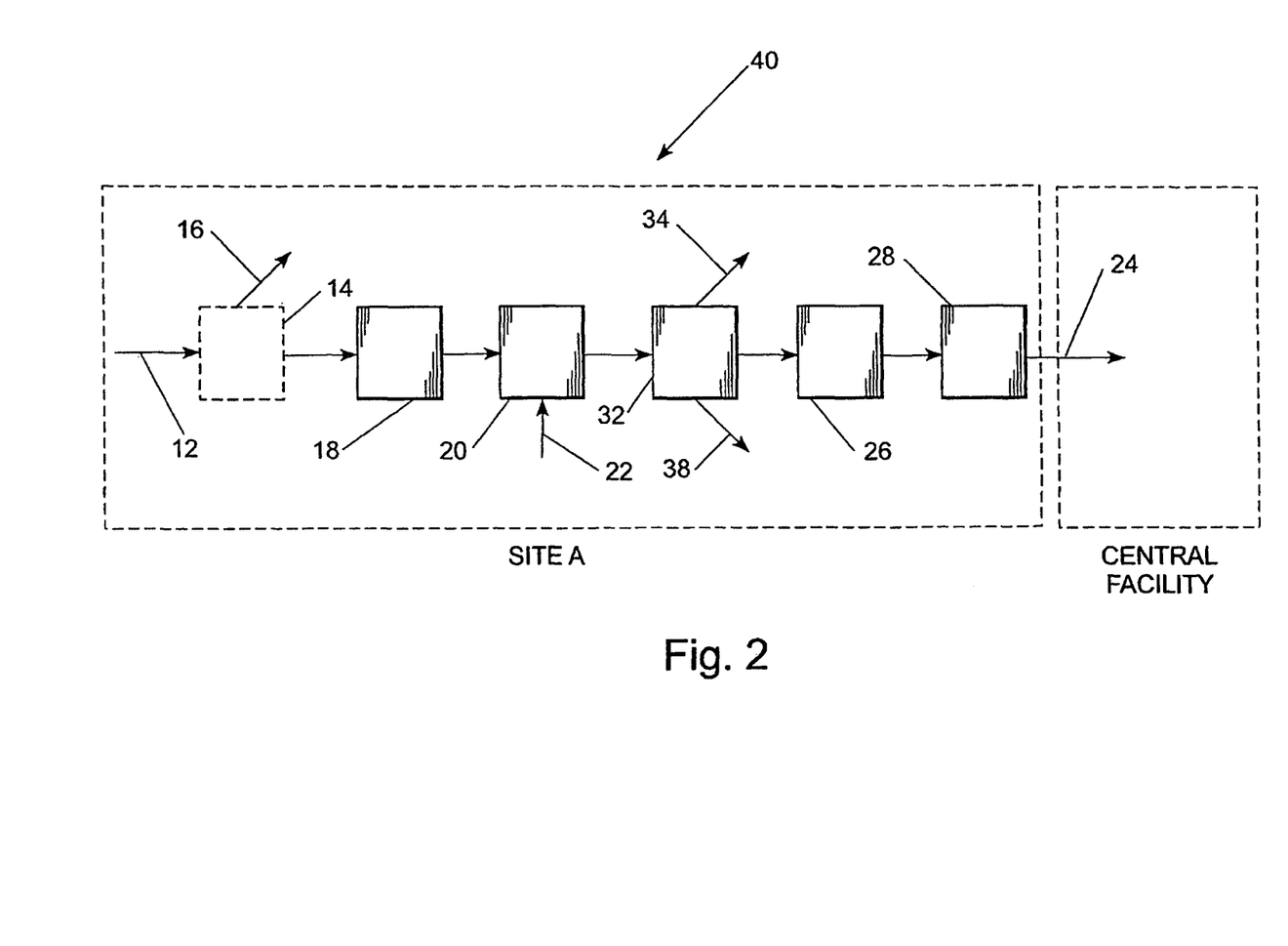
FIG. 2 is a schematic representation of a process of the present invention, in a second embodiment.
Figure 3:
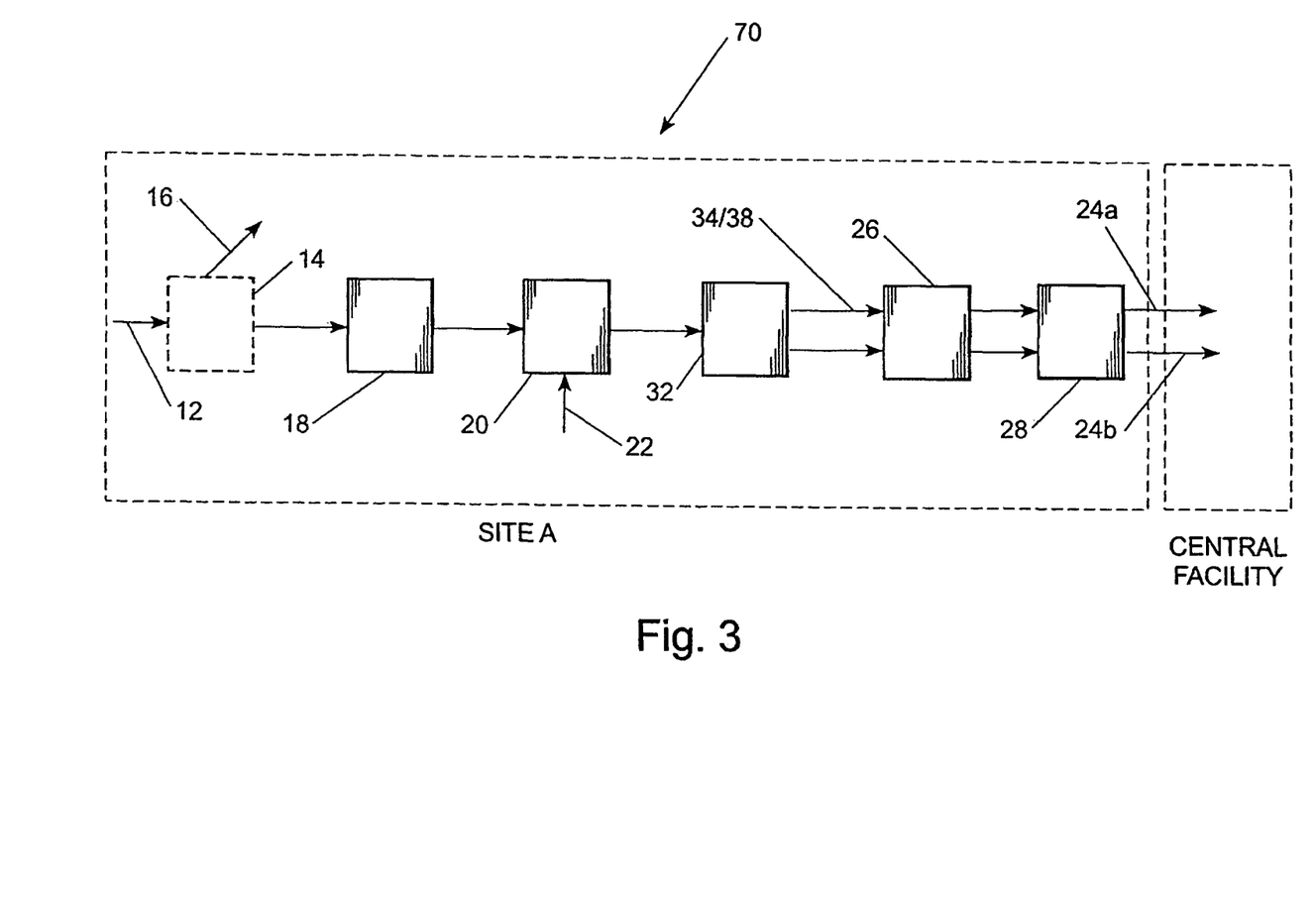
FIG. 3 is a schematic representation of a process according to the present invention, in a variation of the second embodiment.

Higher concentration acid vapors, containing from 70 percent acid up to in excess of 90 percent acid, may be used to substantially solubilize the hemicelluloses as well as lignins in the biomass, the latter being largely insoluble in a 50 percent concentration solution. Embodiments based on substantially solubilizing the hemicelluloses and lignins in the biomass 12 are schematically shown in FIGS. 2 and 3, with features in common amongst the several embodiments shown being given the same reference numbers. These embodiments will be described in greater detail below with reference to FIGS. 2 and 3.

In each of the illustrated embodiments, however, the biomass 12 is preferably permeated with the concentrated acid vapors 22 and maintained in contact with the vapors 22 in acid vapor steeping step 20 for a time and under corresponding conditions of pressure and temperature which are sufficient to at least partly depolymerize or substantially solubilize the lignins and hemicelluloses in the biomass 12, as the case may be. The biomass 12 may be heated before it is placed in contact with the concentrated acid vapors 22, the concentrated acid vapors 22 may be superheated and then applied to the biomass 12, or the vapors 22 and biomass 12 may both be heated together leading into or during the acid vapor steeping step 20. As well, the concentrated acid vapors 22 may be generated in situ, as by application of heat to both the biomass 12 and a concentrated organic acid solution in contact with the biomass 12, or by contact of the concentrated organic acid solution with hot biomass 12.

The conditions of pressure, temperature and residence time necessary to at least partly depolymerize or to substantially solubilize the lignins and hemicelluloses in a given biomass 12 will vary somewhat dependent on the particular biomass being processed and its composition, how finely divided the biomass may be entering the acid vapor steeping step, the particular organic acid or acids selected as well as the concentration of the acid that is used, but generally it is expected that the acid vapor steeping step will be conducted at pressures ranging from atmospheric up to about 500 psig, at temperatures from about 50 degrees Celsius and greater and over a period of time on the order of thirty minutes and greater. Lower concentrations of acid, less severe conditions of temperature and pressure and shorter residence times will be required for the embodiment of FIG. 1, as compared to the embodiments of FIGS. 2 and 3.

Following the acid vapor steeping step 20, the material is dried in step 26 to remove sufficient moisture for allowing the dried partly-processed biomass to then be pelletized in a pelletization or densification step 28. The drying/dewatering step 26 can be accomplished by a number of conventional devices or combinations of such devices for concentrating an aqueous slurry and removing water therefrom to a level suited for pelletization of the remaining solids, for example, centrifuges, hydroclones, belt filter press driers, fluid bed driers, indirect or direct rotary drum driers, spin flash driers and the like. Preferably, the biomass leaving the drying step 26 will have a moisture content of 10 percent or less, more preferably 8 percent or less by weight and most preferably 6 percent or less by weight to facilitate its pelletization and reduce transportation costs.

Pelletization in step 28 can likewise be accomplished using methods and equipment conventionally known to those skilled in the art, as pelletization of animal feeds and of woody biomass for fuels has become well-established, and will preferably result in a material with sufficient cohesiveness and integrity to satisfactorily withstand transport to a second location or central facility 30 by a selected means of transport, whether the material is conveyed pneumatically or by conveyor belts/systems, by truck or rail, by some other means or a combination of means. For convenience; the transport of the pelletized material from Site A to a second location will be described in the claims below and elsewhere herein as "shipping" the material from a local Site A to a second location, and the use of "shipping" is not intended to be limited to ships, planes, trains or trucks or like means of vehicular transport but should be understood as inclusive of any manner in which such pelletized materials may be moved from a Site A to a second location.

In this regard, the pelletized material's needed durability—principally meaning the pellet does not produce an excessive quantity of fines in handling, transport and storage—will depend more particularly on how the material is handled, transported and stored at a given site A, between site A and a given central facility/second location, and at the central facility/second location. As well, there are several devices and related methods which have been developed for assessing pellet durability, so that precise numerical values for durability may not reasonably be assigned a priori. Preferably, however, the pelletized, partially processed biomass in all cases (FIGS. 1-3 and any variations therefrom embraced within the scope of the invention as claimed) will be sufficiently durable so as not to experience more than five percent loss of mass by dusting or fines formation from the completion of the pelletization step 28 to the final disposition of the pelletized material, and preferably not more than three percent of the pelletized, partially processed biomass will be lost as fines in this transition.

The pelletized material 24 may be transported to a second location 30 in the form of a feedlot and used directly as a ruminant feed. Where renewable source-based fuels, fuel additives and/or chemicals are the desired end products, the pelletized, partially processed biomass 24 is then conveniently shipped to the central facility/second location 30 for further processing, which further processing includes at least washing with a solvent or combination of solvents in solvent wash step 32, the solvent(s) being selected to effectively separate the at least partly depolymerized hemicellulosic materials in a product or stream 34 containing pentoses from the hydrolysis of hemicellulosic materials in the biomass, and a predominantly cellulosic solids fraction 36. In FIG. 1, hot water is preferably used in step 32 to separate the substantially water-insoluble lignin and cellulosic fractions from the hemicellulosic fraction, and a more concentrated organic acid wash (in which the partly depolymerized lignins are soluble) and filtration process is used in one or more iterations to finally produce the cellulosic solids fraction 36 and a lignin fraction 38.

In the particular scenario where the pelletized material is desired to be transported to a second location 30 for further processing to yield renewable source-based fuels and fuel additives and/or chemicals, a distributed array of local processing sites around a central plant can be contemplated (a "hub and spoke" concept), wherein typically on average the local processing sites (Sites A) will be 50 kilometers and more removed from the central plant and frequently may be 80 kilometers or more removed from the central plant on average.

Those skilled in the art will of course appreciate that other solvents or combinations of solvents may be beneficially employed as well to effect these separations, for example, an organic co-solvent such as described below with reference to the embodiments of FIGS. 2 and 3 may be used to solubilize and remove residual hemicellulose and lignin materials from the cellulosic solids fraction 36.

Cellulosic solids fraction 36 recovered or fractionated out in this manner can be converted to a hexose product or substantially hexose stream by strong, mineral acid hydrolysis, under conditions suited to carry out this conversion. The hexose product or stream will preferably be comprised substantially entirely of C6 monosaccharides, and of a character suited for upgrading to desired biobased chemical and fuel products with minimal further preprocessing and cleanup. Exemplary biobased chemical and fuel products derivable from the C6 monosaccharides include fuel additive products through hydrogenation and hydrotreating, or ethanol, lysine, threonine, lactic, gluconic or other organic acids through fermentation.

Likewise, the pentose product or stream 34 produced by hydrolysis of the hemicelluloses in a biomass 12 will preferably be comprised substantially entirely of C5 monosaccharides, and of a character suited for upgrading to those biobased chemical and fuel products derivable from such C5 monosaccharides, for example, ethanol, threonine, lysine, lactic, gluconic or other organic acids by fermentation, furfural, furfuryl alcohol, methyl tetrahydrofurfural, furfurylic acid and fuel additives by hydrogenation and hydrotreating.

A preferred strong, mineral acid for hydrolyzing the cellulosic solids fraction 36 is sulfuric acid, applied as a 1 to 80, and preferably 40 to 80, percent concentrated aqueous sulfuric acid solution, at a temperature of from 25 degrees Celsius to 100 degrees Celsius, a pressure of from atmospheric pressure up to 0.7 MPa, gauge (100 psig), and a residence time of 15 minutes to 2 hours dependent primarily on the temperature conditions used.

The lignins fraction 38 can in like manner be put to practical further use, for example, through ozonolysis to an aromatic fuel additive based, for example, on the teachings of United States Published Patent Application No. 2009/0718498A1, as a gasification feed for producing synthesis gas, as a combustion fuel, or through ozonoylsis to produce an aromatic sulfonation feed for producing biobased linear alkylbenzene sulfonates.

Turning now to FIG. 2, an alternate embodiment is shown schematically. In the embodiment 40, only the cellulosic fraction from the biomass 12 is included in the pelletized material 24 that is shipped to a central facility 30 for further processing to a ruminant feed material or to a hexose product or stream for biobased fuels, fuel additives or chemicals, while the hemicellulosic and lignin fractions are hydrolyzed at a first site, Site A, that is preferably convenient to where the biomass has been produced or grown.

In the embodiment 40 of FIG. 2 as well as the embodiment 70 of FIG. 3, as has been discussed previously, the hemicelluloses and lignins are preferably dissolved as much as possible in a solvent including one or more weak organic acids (formic or acetic acids again being preferred) in order to produce a clean cellulosic solids pulp that can be dried, pelletized and shipped for further processing at a central facility or used in an animal feed. Thus, in addition to using a higher concentration hot acid vapor stream 22 for the acid vapor steeping step 20, comprised of from 70 percent to in excess of 90 percent of acid, preferably an organic co-solvent is employed with additional concentrated acid solution through one or more iterations of washing/dissolution and filtration in solvent wash step 32.

For the embodiment 40 shown in FIG. 2, the lignins and hemicelluloses solubilized in the filtrate in this manner can then be separated at Site A into streams or products 38 and 34 as described in the embodiment 10, and the remaining cellulosic solids fraction dried and pelletized in corresponding steps 26 and 28 for transport as stream or product 24 to a second location/central facility for use in an animal feed or for the further processing described above for FIG. 1.

For the embodiment 70 shown in FIG. 3, the filtrate containing so much of the hemicelluloses and lignins as have been solubilized in the washings and filtrations accomplished in step 32 can be evaporated in parallel to the cellulosic solids in step 26, and the solids produced through precipitation can themselves be pelletized in step 28 and transported to the second location/central facility or stored for further use and/or processing at Site A at a later time. Thus, two pelletized products are provided in FIG. 3, the cellulosic component of the biomass 12 largely being accounted for in a pelletized product 24b and hemicellulosic and lignin components of the biomass 12 being largely accounted for in pelletized product 24a, though in this regard those skilled in the art (and familiar with fractionation methods) will certainly appreciate that in each of the embodiments 10, 40 and 70 the pelletized product 24a will likely contain some of the cellulosic materials originally found in the biomass 12 and the pelletized product 24b will likely contain some especially higher molecular weight hemicellulosic and lignin materials.

The pentose (from acid hydrolysis of hemicelluloses in the biomass 12 in steps 20 and 32) and lignin components found in the pelletized product 24a can at the second location/central facility then be used in animal feed or separated in products or streams 34 and 38, respectively, for example through one or more iterations of washing and filtration of the solids 24a with hot water or some other suitable solvent at the second location/central facility.

The cellulosic solids in material 24 in FIG. 2 or material 24b in FIG. 3 can be used or further processed in the manner described for cellulosic solids fraction 36 in FIG. 1, and the pentoses found in stream or product 34 as well as the lignins contained in stream or product 38 can likewise be used or further processed as previously described in conjunction with FIG. 1.

While, as noted above, concentrated formic acid has been known to be effective at dissolving and separating out both the lignin and hemicellulose components from the cellulose component of a lignocellulosic biomass in the pulp and paper industry, the particulars of using concentrated formic acid for this purpose in a pulpmaking context are such that one could not feasibly apply the same or a similar process in the context of fractionating a lignocellulosic biomass in order to develop feeds for the manufacture of renewable source-based fuels, fuel additives and/or chemicals. In making pulp from a biomass using concentrated formic acid, very considerable energy is required for heating large enough amounts of formic acid and water to generate the pulp slurry, and removal and recovery of the formic acid in high enough concentrations for solvent recycle is difficult and costly due to the formation of azeotropes with water, acetic acid and formic acid.

In the context of the present invention, however, where formic acid is used as the organic acid, by employing just enough formic acid in vapor form to thoroughly wet the biomass and to either partly polymerize or substantially solubilize the lignin and hemicelluloses therein (as the case may be), the formic acid concentration in the materials evaporated off in a drying step 26 relative to water can be kept essentially the same as in the acid vapor steeping step 20 and the whole may accordingly be condensed, recycled and reused for the stream 22, avoiding the energy-intensive and costly azeotropic distillation recovery methods associated with the known formic acid pulping processes. As well, with the objective in mind of producing a material with at least partly depolymerized or substantially solubilized hemicelluloses and lignins that contains just enough residual moisture to enable good pelletization, versus producing a solids slurry for making paper, much smaller amounts of water and of formic acid are required generally so that the energy requirements are correspondingly much reduced.

Whether formic acid is used alone or in combination with other weak organic acids in a process according to the present invention, or whether another weak organic acid is used that does not form an azeotrope with water, the amount of acid that may be employed may be insufficient in fact to justify the expense of any recovery and recycle, so that neutralization may be preferred. However, where acid recovery and recycle are desired, those skilled in the art will be well able to select and employ suitable means for doing so—both by recovering and recycling the materials evaporated in a drying step 26, and by recovering and recycling weak organic acid from eventual pentose and hexose streams from further processing. In the latter case, where acetic acid is used instead of formic acid, the acetic acid can be recovered by simple distillation. Where formic acid is used, azeotropic distillation may be employed, or when the formic acid is applied at a very high concentration with small amounts of steam, the acid can be recovered, recycled and reused in concentrated form by simple distillation without the need of separating out the included water. We have found in this circumstance that certain organic co-solvents identified as useful for completing the solubilization and separation of the hemicelluloses and lignins from the cellulosic solids, also act as effective entrainers for the simple distillation and recovery of formic acid. Suitable organic co-solvents we have identified include ethyl formate, ethyl lactate and hydroxymethyl tetrahydrofuran, ethyl formate being preferred.

Those skilled in the art will appreciate that while preferred embodiments of the invention have been described herein, numerous variations and alternatives can in like manner be conceived. For example, enzymes can be used alongside an acid to hydrolyze the hemicellulosic and cellulosic fractions of a biomass. Where silage is used for the biomass, anaerobic fermentation of the silage itself over a period of time produces lactic acid, and this lactic acid can be used as a weak organic acid in the acid vapor steeping step 20. Still other variations will be evident to those skilled in the art, which do not depart from the true scope of the present invention, as expressed in the claims which follow.

What is claimed is:

1. A method of processing a lignocellulosic biomass including cellulose, hemicellulose and lignin fractions, comprising the steps of:
   forming a concentrated organic acid vapor biomass treating material comprising water and at least 50 percent by weight of one or more organic acids;
   then applying the concentrated organic acid vapors treating material to the biomass for a time and under conditions sufficient to a least partly depolymerize the hemicellulosic and lignin materials in the biomass;
   if needed, drying the thus treated biomass to provide a sufficiently high solids content material as to be pelletized; and
   pelletizing the concentrated organic vapor-treated material.

2. A method according to claim 1, wherein the pelletized material is used in a ruminant feed.

3. A method according to claim 1, wherein a cellulosic solids product is recovered from the pelletized material by solvent washing the pelletized material in one or more iterations with filtration, whereby the at least partly depolymerized hemicellulosic and lignin materials from the pelletized material are separated together from the remaining cellulosic solids.

4. A method according to claim 3, further comprising, in one or more iterations, washing the at least partly depolyinerized hemicellulosic and lignin materials with filtering to separate water-insoluble lignin solids from water-soluble hemicellulosic materials.

5. A method according to claim 1, wherein the at least partly depolymerized hemicellulosic materials are separated from the pelletized material by water washing the pelletized material in one or more iterations with filtration, and the lignins are subsequently separated from the remainder of the pelletized material by a separate solvent wash with filtration, also in one or more iterations.

6. A method according to either of claim 4 or 5, comprising a further acid hydrolysis step conducted on the at least partly depolymerized hemicellulosic materials after the at least partly depolymerized hemicellulosic materials have been separated from the lignins and the remainder of the pelletized material.

7. A method according to claim 6, further comprising fermenting the product of the further acid hydrolysis of the hemicellulosic materials to produce ethanol, lysine, threonine, lactic, gluconic or other organic acids, or hydrogenating and hydrotreating the product of the further acid hydrolysis step to yield a fuel additive product for transportation fuels.

8. A method according to either of claim 4, wherein the water-insoluble lignins are subjected to ozonolysis or exposure to one or more other oxidants, or combusted as a fuel, or supplied to a coking process for making a liquid hydrocarbon product and coke, or fed to a gasifier for producing a synthesis gas.

9. A method according to claim 3, wherein the cellulosic solids are contacted with a strong mineral acid to hydrolyze the cellulosic solids and provide a hexose product or stream, and the hexose product or stream is fermented to produce ethanol, lysine, threonine, lactic, gluconic or other organic acids.

10. A method according to claim 1, wherein the lignocellulosic biomass is characterized as having, an acid-detergent insoluble lignin content of 6 percent or greater by weight, on a dry weight basis.

11. A method according to claim 10, wherein the lignocellulosic biomass is comprised one or more of a mature grass, grain crop residue separately or contained in a silage, corn stover, wheat straw, barley straw, miscanthus specie, switchgrass, bahia grass, sorghum specie, sugar cane bagasse, orchardgrass, reed canarygrass and cotton gin trash.

12. A method according to claim 11. wherein the lignocellulosic biomass processed comprises corn stover and corn fiber.

13. A method according to claim 12, wherein the lignocellulosic biomass processed is ensiled whole plant corn, and wherein the biomass is preprocessed before the concentrated organic acid vapor biomass treating material is applied to isolate and remove at least one cog of the ensiled whole plant corn.

14. A method according to claim 13, wherein corn oil is recovered from the ensiled whole plant corn biomass before the same is contacted with the concentrated organic acid vapor biomass treating material.

15. A method according to claim 13, wherein the leaf fraction of corn stover is isolated and removed mechanically from the ensiled whole plant corn biomass before the same is contacted with the concentrated organic acid vapor biomass treating material.

16. A method according to claim 13, wherein one or more components which are higher in sulfur, nitrogen or ash content are mechanically isolated and removed from the ensiled whole plant corn biomass is contacted with the concentrated organic acid vapor biomass treating material.

17. A method according to claim 1, wherein the concentrated organic acid vapor biomass treating material is applied to the biomass at an elevated temperature of 50 degrees Celsius or greater.

18. A method according to claim 17, wherein the concentrated organic acid vapor biomass treating material consists of one or more of acetic, propionic, malic, succinic, formic and lactic acids in combination with water, and the concentrated acid vapor biomass treating material is applied at a temperature of from 50 degrees Celsius to 160 degrees Celsius, a pressure of from atmospheric pressure to 3.5 MPa, gauge, and for a time period of 30 minutes and more.

19. A method according to claim 17, wherein the concentrated organic acid vapor biomass treating material contains 50 percent by weight and greater of formic or acetic acid or a combination of formic and acetic acids, with the balance being water.

20. A method according to either of claims 18 or 19, wherein the concentrated organic acid vapor biomass treating material contains 70 percent or more by weight of the one or more acids, with the balance of water.

21. A method according to claims 1, wherein the organic acid-treated biomass is dried to a moisture content of 10 percent or less by weight.

22. A method according to claim 20, wherein the dried biomass is pelletized without the addition of a further binder.

23. A method according to claim 1, wherein the organic acid vapor treatment, drying and pelletizing steps are applied at a plurality of locations for shipment of pelletized material to a common second location.

24. A method according to claim 23, wherein the plurality of sites are on average a distance of 50 kilometers or more from the common second location.

25. A method according to claim 24, wherein the plurality of sites are on average a distance of 80 or more kilometers from the common second location.

26. A method according to claim 22, wherein the organic add vapor treatment, drying and pelletizing steps are applied to produce a pelletized material at a location that is at least 50 kilometers from the second location.

27. A method according to claim 1, further comprising processing the biomass before contact with the concentrated organic acid vapor biomass treating material to isolate and remove at least one component of the biomass that is higher in protein and suitable for use in or for an animal feed, or that has a higher than desired sulfur, nitrogen or ash content.

28. A method of processing a lignocellulosic biomass including cellulose, hemicellulose and lignin fractions, comprising the steps of:
  forming a concentrated organic acid vapor biomass treating material comprising water and one or more organic acids selected from acetic, propionic, malic, succinic formic and lactic acids;
  then applying the concentrated organic acid vapor biomass treating material to the biomass for a time and under conditions which are sufficient to substantially solubilize hemicellulosic and lignin materials in the biomass;
  in one or more iterations, washing the treated biomass with a solvent or solvent mixture and filtering to separate hemicellulosic and lignin materials in the filtrate and cellulosic materials as a solid residue;
  if needed, drying the solid residue to provide a sufficiently high solids content material as to be pelletized; and
  pelletizing the concentrated organic vapor-treated material.

29. A method according to claim 28, further comprising, in one or more iterations, water washing the hemicellulosic and lignin materials in the filtrate with additional filtering to separate water-insoluble lignin solids from water-soluble hemicellulosic materials.

30. A method according to claim 28, wherein a concentrated formic, acetic or formic/acetic acid vapor biomass treating material is applied to the biomass at a temperature of from 50 degrees Celsius to 160 degrees Celsius, a pressure of from atmospheric pressure to 3.5 MPa, gauge, and for a time period of 30 minutes and more.

31. A method according to claim 30, wherein the concentrated organic acid vapor biomass treating material is 70 percent by weight and greater of the organic acid or acids, with the balance being water.

32. A method according to claim 1, wherein the concentrated organic acid vapor biomass treating, material is 90 percent by weight and greater of the organic acid or acids, with the balance being water.

33. A method according to claims 28-32, wherein the material evaporated off in drying the solid residue is collected and recycled to the organic acid vapor treatment step without a preceding separation of the organic acid or acids and water contained in such material.

34. A method according to claim 28, further comprising preprocessing the biomass before contact with the concentrated organic acid vapor biomass treating material to isolate and remove at least one component of the biomass that is higher in protein and suitable for use in or for an animal feed, or that has a higher than desired sulfur, nitrogen or ash content.

35. A method according to claim 28, further comprising: drying the filtrate containing the substantially solubilized hemicelluloses and lignins to provide a sufficiently high solids content material as to be pelletized, and pelletizing the resulting material.

36. A method according to claim 28, wherein the lignocellulosic biomass is characterized as having an acid detergent-insoluble lignin content of 6 percent or greater by weight.

* * * * *